United States Patent [19]
Umemura et al.

[11] 3,981,919
[45] Sept. 21, 1976

[54] RACEMIZATION OF OPTICALLY ACTIVE ALLETHROLONE

[75] Inventors: Takeaki Umemura, Takarazuka; Fukashi Horiuchi, Kawani, both of Japan

[73] Assignee: Sumitomo Chemical Company, Limited, Osaka, Japan

[22] Filed: Jan. 22, 1975

[21] Appl. No.: 542,904

[30] Foreign Application Priority Data
Jan. 25, 1974 Japan.............................. 49-11314

[52] U.S. Cl.......................... 260/586 R; 260/DIG. 7
[51] Int. Cl.$^2$.................. C07C 45/00; C07B 20/00; C07C 29/00
[58] Field of Search.................... 260/586 R, DIG. 7

[56] References Cited
UNITED STATES PATENTS

| | | | |
|---|---|---|---|
| 2,891,888 | 6/1959 | Guest et al...................... | 260/586 R |
| 3,720,703 | 3/1973 | Elliot et al...................... | 260/586 R |

OTHER PUBLICATIONS
Ehel, "Stereochemistry of Carbon Compounds," pp. 31–47, (1962).

*Primary Examiner*—Norman Morgenstern
*Attorney, Agent, or Firm*—Wenderoth, Lind & Ponack

[57] ABSTRACT

A process is provided for preparing racemic allethrolone which comprises reacting (−) allethrolone with phosphorus chloride compounds in the presence of a Lewis acid, and hydrolyzing the racemic 4-chloroallethrone thus obtained.

8 Claims, No Drawings

RACEMIZATION OF OPTICALLY ACTIVE ALLETHROLONE

The present invention relates to a racemization process of optically active allethrolone characterized in that optically active allethrolone is converted to the corresponding racemic chloro-derivative, (±) 4-chloro-allethrone, and then the chloro-derivative is reconverted to racemic allethrolone by hydrolyzing reaction.

Allethrolone is an alcohol moeity of the cyclopropanecarboxylic acid esters which are an active ingredient of pyrethroid insecticides, for example allethrin which is useful as a low-toxic insecticide, and exists in two optical isomers, (+) and (−) isomers. Of the two isomers, a pyrethroid insecticide having in its alcohol moiety the (+) isomer is much superior to that of the other isomer in efficacy.

It is well known from Belgian Patent No. 793,190 (1971) and Japanese Open Patent Publication No. 75,545/1973 that (±) allethrolone can be resolved into the two optically active isomers by treating (±) allethrolone half-esters as an intermediate, for example (±) allethrolone acid succinate and (±) allethrolone acid phthalate, with optically active bases such as ephedrine and α-phenyl-β-(p-tolyl)-ethylamine.

But, the resolution by this well-known method not only produces (+) allethrolone which is useful as the alcohol moiety, but also produces (−) allethrolone as a by-product which ester is much inferior in insecticidal activity, and so it has no industrial value. Therefore, re-conversion of the useless (−) allethrolone to valuable (+) allethrolone or (±) allethrolone has a large industrial significance.

An object of the present invention is to provide an economical, industrially advantageous recemization process of (−) allethrolone.

According to the process of the present invention, in the first reaction step, (−) allethrolone is converted to almost completely racemized 4-chloro-allethrone by reacting with phosphorus chloride compounds, for example phosphorus trichloride, phosphorus pentachloride, phosphorus oxychloride, triphenyl phosphite.dichloride $(C_6H_5O)_3PCl_2$, diphenyltrichlorophosphorane $(C_6H_5)_2PCl_3$, and triphenylphosphine.dichloride. $(C_6H_5)_3PCl_2$, in the presence of Lewis acids such as zinc chloride and boron trifluoride.etherate.

In the second step, the racemic 4-chloro-allethrone thus obtained can be re-converted to the almost completely racemized allethrolone with ease and in a high yield by hydrolyzing the said 4-chloro-allethrone in the presence of weak bases, for example calcium carbonate, to remove hydrogen chloride produced during the hydrolysis, or by catalytically hydrolyzing the said 4-chloro-allethrone in the presence of silver ion or mercury ion (specifically silver nitrate or mercury halide).

The preparation of the racemic 4-chloro-allethrone from (±) allethrolone is already well known in Casida et al., J. Agr. Food Chem., 17, 931 (1969). But, chlorination of optically active allethrolone according to this well-known method produces respectively optically active 4-chloro-allethrone which is hydrolyzed into allethrolone retaining an optical rotation of the same direction as that of the original allethrolone to a considerable extent. Consequently, the object of the present invention can not be achieved (refer to the Reference example).

For the recemization process of optically active allethrolone via 4-chloro-allethrone, therefore, it is particularly essential to prepare almost completely racemized 4-chloro-allethrone as an intermediate. For this purpose, the above-mentioned chlorination using phosphorus chloride compounds in the presence of Lewis acid is particularly effective.

The solvent used for the chlorination includes inert solvents such as ether, benzene, toluene, dioxane, chloroform and mixture thereof. The reaction temperature is −20°C. to 110°C., but it is preferred to carry out the chlorination so that the temperature is kept at −10°C. to 10°C. at the beginning of the reaction as the reaction is generally exothermic, and then is raised to above room temperature to complete the reaction. The solvent used for the hydrolysis includes water or a mixture of water and organic solvents miscible with water, for example acetone, dioxane, tetrahydrofuran and a mixture thereof. The temperature at which the hydrolysis is carried out is preferably from room temperature to refluxing temperature of the reaction solvent.

The present invention will be illustrated with reference to the following examples, which are only given for the purpose of illustration and not to be interpreted as limiting thereto.

EXAMPLE 1

In 30 ml. of dry benzene were dissolved 4.8 g. (0.035 mole) of phosphorus trichloride, and then 13.9 g. (0.102 mole) of zinc chloride were added thereto under ice-cooling. Then, a benzene solution containing 15.2 g. (0.1 mole) of (−) allethrolone ($[\alpha]_D^{22} = -4.64°$ in ethanol) was gradually added dropwise to the resulting solution while stirring. After the dropwise addition, the reaction solution was stirred for further 1 hour under ice-cooling, raised to room temperature and then continued to stir to the end of reaction. Thereafter, the solution was poured into ice-water and extracted with benzene. The benzene layer was washed with a 5 % aqueous sodium carbonate solution and then water, dried over anhydrous sodium sulfate and distilled under reduced pressure to obtain 12.6 g. of 4-chloro-allethrone (b.p. 62° – 65°C./0.4 mmHg). Yield 74 %, $[\alpha]_D^{21} = -0.04°$ (chloroform) and $n_D^{19} = 1.5188$.

EXAMPLE 2

A mixture of 3.39 g. (0.02 mole) of 4-chloro-allethrone obtained in Example 1, 1.10 g. (0.011 mole) of calcium carbonate and 20 ml. of water was heated under reflux for 4 hours. Then, after cooling, sodium chloride was added to the reaction solution to saturate the aqueous layer followed by extraction with ether. The ether layer was dried over anhydrous sodium sulfate and distilled under reduced pressure to obtain 2.29 g. of allethrolone (b.p. 102° – 105°C./0.5 mmHg). Allethrolone thus obtained was completely consistent with the authentic sample of allethrolone in the infra-red absorption spectrum and nuclear magnetic resonance spectrum. Yield 75 %, $[\alpha]_D^{22} = \pm0°$ (ethanol) and $n_D^{19} = 1.5176$.

EXAMPLE 3

To 3.39 g. (0.02 mole) of 4-chloro-allethrone obtained in Example 1 were added 40 ml. of an aqueous solution containing 1.54 g. (0.022 mole) of silver nitrate, and the resulting solution was stirred in the dark. After the reaction was completed, sodium chloride was added to the reaction solution to saturate the aqueous layer followed by extraction with ether. The ether layer was dried over anhydrous sodium sulfate and distilled under reduced pressure to obtain 1.70 g. of allethrolone (b.p. 105° – 107°C./0.3 mmHg). Allethrolone thus obtained was completely consistent with the authentic sample of allethrolone in the infra-red absorption spectrum and nuclear magnetic resonance spectrum. Yield 56 %, $[\alpha]_D^{22} = \pm 0°$ (ethanol) and $n_D^{19} = 1.5168$.

EXAMPLE 4

In 30 ml. of dry ether were dissolved 15.5 g. (0.101 mole) of phosphorus oxychloride, and then 13.9 g. (0.102 mole) of zinc chloride were added thereto under ice-cooling. Then an ether solution containing 15.2 g. (0.1 mole) of (−) allethrolone ($[\alpha]_D^{22} = -4.64°$ in ethanol) was gradually added dropwise to the resulting solution while stirring. After the dropwise addition, the reaction solution was stirred for further 1 hour under ice-cooling, raised to room temperature and then continued to stir to the end of reaction. Thereafter, the solution was poured into ice-water and extracted with ether. The ether layer was washed with a 5 % aqueous sodium carbonate solution and then water, dried over anhydrous sodium sulfate and distilled under reduced pressure to obtain 13.5 g. of 4-chloro-allethrone (b.p. 60° – 65°C./0.5 mmHg). Yield 80 %, $[\alpha]_D^{21.5} = -1.03°$ (chloroform) and $n_D^{19} = 1.5165$.

EXAMPLE 5

Hydrolysis of 3.39 g. (0.02 mole) of 4-chloro-allethrone obtained in Example 4 was carried out in the same manner as described in Example 2 to obtain 2.46 g. of allethrolone (b.p. 110° – 115°C./0.7 mmHg). Allethrolone thus obtained was completely consistent with the authentic sample of allethrolone in the infra-red absorption spectrum and nuclear magnetic resonance spectrum. Yield 81 %, $[\alpha]_D^{21} = -0.03°$ (ethanol) and $n_D^{19} = 1.5175$.

EXAMPLE 6

In 30 ml. of dry ether were dissolved 2.19 g. (0.0105 mole) of phosphorus pentachloride, and then 6.95 g. (0.051 mole) of zinc chloride were added thereto under ice-cooling. Then, an ether solution containing 7.61 g. (0.05 mole) of (−) allethrolone ($[\alpha]_D^{22} = -4.64°$ in ethanol) was gradually added dropwise to the resulting solution while stirring. After the dropwise addition, the reaction solution was stirred for further 1 hour under ice-cooling, raised to room temperature and then continued to stir to the end of reaction. Thereafter, the solution was poured into ice-water and extracted with ether. The ether layer was washed with a 5 % aqueous sodium carbonate solution and then water, dried over anhydrous sodium sulfate and distilled under reduced pressure to obtain 6.00 g. of 4-chloro-allethrone (b.p. 70° – 72°C./0.8 mmHg). Yield 71 %, $[\alpha]_D^{21} = -0.64°$ (chloroform) and $n_D^{19} = 1.5175$.

EXAMPLE 7

Hydrolysis of 3.39 g. (0.02 mole) of 4-chloro-allethrone obtained in Example 6 was carried out in the same manner as described in Example 2 to obtain 2.13 g. of allethrolone (b.p. 113° – 115°C./1 mmHg). Allethrolone thus obtained was completely consistent with the authentic sample of allethrolone in the infra-red absorption spectrum and nuclear magnetic resonance spectrum. Yield 70 %, $[\alpha]_D^{21} = \pm 0°$ (ethanol) and $n_D^{19} = 1.5171$.

EXAMPLE 8

In 30 ml. of dry benzene were dissolved 2.40 g. (0.0175 mole) of phosphorus trichloride, and then 7.24 g. (0.051 mole) of borontrifluoride.etherate were added thereto under ice-cooling. Then, a benzene solution containing 7.61 g. (0.05 mole of (−allethrolone ($[\alpha]_D^{22} = -4.64°$ in ethanol) was gradually added dropwise to the resulting solution while stirring. After the dropwise addition, the reaction solution was stirred for further 1 hour under ice-cooling, raised to room temperature and then continued to stir to the end of reaction. Thereafter, the reaction solution was poured into ice-water and extracted with benzene. The benzene layer was washed with a 5 % aqueous sodium carbonate solution and then water, dried over anhydrous sodium sulfate and distilled under reduced pressure to obtain 4.62 g. of 4-chloro-allethrone (b.p. 58° – 60°C./0.35 mmHg). Yield 55 %, $[\alpha]_D^{22} = -10.6°$ (chloroform) and $n_D^{19} = 1.5160$.

EXAMPLE 9

Hydrolysis of 3.39 g. (0.02 mole) of 4-chloro-allethrone obtained in Example 8 was carried out in the same manner as described in Example 2 to obtain 2.03 g. of allethrolone (b.p. 102° – 106°C./0.3 mmHg). Allethrolone thus obtained was completely consistent with the authentic sample of allethrolone in the infra-red absorption spectrum and nuclear magnetic resonance spectrum. Yield 67 %, $[\alpha]_D^{21} = -0.08°$ (ethanol) and $n_D^{19} = 1.5167$.

REFERENCE EXAMPLE 1

In 5 ml. of dry benzene were dissolved 4.8 g. (0.035 mole) of phosphorus trichloride, and then 1.5 g. of pyridine was added thereto under ice-cooling. Then, a mixture of 0.5 g. of pyridine and 15.2 g. (0.1 mole) of (−) allethrolone ($[\alpha]_D^{22} = -4.86°$ in ethanol) was gradually added dropwise to the resulting solution while stirring. After the dropwise addition, the reaction solution was stirred for further 1 hour under ice-cooling, raised to room temperature and then continued to stir to the end of reaction. Thereafter, the reaction solution was poured into ice-water and extracted with benzene. The benzene layer was washed with a 5 % aqueous sodium carbonate solution and then water, dried over anhydrous sodium sulfate and distilled under reduced pressure to obtain 9.6 g. of 4-chloro-allethrone (b.p. 64° – 65°C./0.6 mmHg). Yield 64 %, $[\alpha]_D^{22} = -82.9°$ (chloroform) and $n_D^{28.5} = 1.5134$.

REFERENCE EXAMPLE 2

Hydrolysis of 2.54 g. (0.015 mole) of 4-chloro-allethrone obtained in Reference Example 1 was carried out in the same manner as described in Example 2 to obtain 1.60 g. of allethrolone (b.p. 105° – 107°C./0.3 mmHg). Allethrolone thus obtained was completely consistent with the authentic sample of allethrolone in the infra-red absorption spectrum and nuclear magnetic resonance spectrum. Yield 70 %, $[\alpha]_D^{22} = -1.76°$ (ethanol) and $n_D^{25} = 1.5145$.

REFERENCE EXAMPLE 3

Hydrolysis of 1.70 g. (0.01 mole) of 4-chloro-allethrone obtained in Reference Example 1 was carried out in the same manner as described in Example 3 to obtain 0.9 g. of allethrolone (b.p. 105° – 107°C./0.3 mmHg). Allethrolone thus obtained was completely consistent with the authentic sample of allethrolone in the infra-red absorption spectrum and nuclear magnetic resonance spectrum. Yield 59 %, $[\alpha]_D^{21} = -3.36°$ (ethanol) and $n_D^{25} = 1.5141$.

What we claim is:

1. A process for preparing racemic allethrolone which comprises reacting (−) allethrolone with a phosphorus chloride compound selected from the group consisting of phosphorus trichloride, phosphorus pentachloride, phosphorus oxychloride, triphenylphosphite dichloride, diphenyltrichlorophosphorane, and triphenylphosphine dichloride, in the presence of a Lewis acid, separating the 4-chloro-allethrolone and hydrolyzing racemic 4-chloro-allethrolone thus obtained in the presence of a weak base.

2. The process according to claim 1, wherein the Lewis acid is a member selected from the group consisting of zinc chloride and borontrifluoride etherate.

3. The process according to claim 1, wherein the chlorinating reaction is carried out in the presence of a solvent at a temperature between −20°C. and 110°C.

4. The process according to claim 3, wherein the solvent is a member selected from the group consisting of ether, benzene, toluene, dioxane, chloroform and a mixture thereof.

5. The process according to claim 3, wherein the temperature is between −10°C. and 10°C.

6. The process according to claim 1, wherein the hydrolysis is carried out in the presence of a solvent.

7. The process according to claim 6, wherein the solvent is water or a mixture of water and organic solvents miscible with water.

8. The process according to claim 7, wherein the organic solvent is a member selected from the group consisting of acetone, dioxane, tetrahydrofuran and a mixture thereof.

* * * * *